US008885031B2

(12) United States Patent
Kato

(10) Patent No.: US 8,885,031 B2
(45) Date of Patent: Nov. 11, 2014

(54) ENDOSCOPE SYSTEM WHICH STABILY SUPPLIES HIGHLY ACCURATE CLOCKS TO A DISTAL END PORTION

(75) Inventor: Shuichi Kato, Tokyo (JP)

(73) Assignee: Olympus Corporation, Tokyo (JP)

( * ) Notice: Subject to any disclaimer, the term of this patent is extended or adjusted under 35 U.S.C. 154(b) by 410 days.

(21) Appl. No.: 13/117,725

(22) Filed: May 27, 2011

(65) Prior Publication Data

US 2011/0292194 A1 Dec. 1, 2011

(30) Foreign Application Priority Data

May 31, 2010 (JP) ................................ P2010-124663

(51) Int. Cl.
*H04N 9/47* (2006.01)
*A61B 1/045* (2006.01)
*A61B 1/00* (2006.01)

(52) U.S. Cl.
CPC ............. *A61B 1/00009* (2013.01); *A61B 1/045* (2013.01); *A61B 1/00045* (2013.01)
USPC ........................................................ 348/65

(58) Field of Classification Search
CPC .................................................. A61B 1/00045
USPC ........................................................ 348/65
See application file for complete search history.

(56) References Cited

U.S. PATENT DOCUMENTS

| | | | |
|---|---|---|---|
| 2002/0145661 A1* | 10/2002 | Takahashi et al. | 348/65 |
| 2002/0179712 A1* | 12/2002 | Yahagi et al. | 235/454 |
| 2009/0058997 A1* | 3/2009 | Kato | 348/65 |
| 2009/0213212 A1* | 8/2009 | Nakamura | 348/65 |
| 2009/0290018 A1* | 11/2009 | Abe | 348/76 |
| 2010/0125165 A1* | 5/2010 | Torii et al. | 600/106 |

FOREIGN PATENT DOCUMENTS

| | | |
|---|---|---|
| JP | 07-194526 A | 8/1995 |
| JP | 10-215153 A | 8/1998 |
| JP | 2004-221962 A | 8/2004 |
| JP | 2007-260066 A | 10/2007 |
| JP | 2008-154934 A | 7/2008 |
| JP | 2009-045113 A | 3/2009 |
| JP | 2010-075319 A | 4/2010 |

OTHER PUBLICATIONS

Office Action dated Dec. 3, 2013, issued in corresponding Japanese application No. 2010-124663, w/ English translation.

* cited by examiner

*Primary Examiner* — Dave Czekaj
*Assistant Examiner* — Leron Beck
(74) *Attorney, Agent, or Firm* — Westerman, Hattori, Daniels & Adrian, LLP

(57) ABSTRACT

This endoscope system includes: a distal end portion which is inserted inside a specimen and which has an imaging section that creates video signals, a video signal processing section that processes the video signals, a video transmitting section that transmits the processed video signals, a timing signal creation section that creates a timing signal needed to drive the imaging section, the video signal processing section, or the video transmitting section, and a base clock receiving section that receives as an optical signal a base clock which is the basis of the timing signal and then converts the received optical signal into an electrical signal; and an external apparatus having an insertion portion which guides the distal end portion into the specimen, a monitor that displays the video signals, and a video processor that processes the video signals from the distal end portion and outputs them to the monitor.

14 Claims, 8 Drawing Sheets

ENDOSCOPE SYSTEM WHICH STABILY SUPPLIES HIGHLY ACCURATE CLOCKS TO A DISTAL END PORTION

BACKGROUND OF THE INVENTION

1. Field of the Invention

The present invention relates to an endoscope system in which an imaging section is inserted into an object.

Priority is claimed on Japanese Patent Application No. 2010-124663, filed May 31, 2010, the contents of which are incorporated herein by reference.

2. Description of Related Art

In typical circuit systems, an oscillator (which is formed by a crystal oscillator or the like and outputs a highly accurate clock) is provided near to a timing generator which generates timing signals for the circuit, and a clock from this oscillator are used for the base clock which provides the basis of these timing signals. By placing the oscillator close to the timing generator, the base clock can be kept at a high level of accuracy, and it is possible to generate stable timing signals.

In contrast to this, in electronic endoscope systems, in order to make the portion which is inserted inside an organism (i.e., the distal end portion) thinner, and also in order to decrease the power consumption of the distal end portion (i.e., of the distal end portion circuit) and thereby inhibit heat generation, oscillators having oversize packaging and high power consumption are not positioned at the distal end portion. In electronic endoscope systems, it is normal for the oscillator and the distal end portion to be located apart from each other and for a clock to be transmitted from the oscillator to the distal end portion by means of fine-wire coaxial cable, and for this clock to then be used for the base clock of the timing generator of the distal end portion.

However, as the definition of imaging elements has become higher in recent years, the frequency of the timing signals required at the distal end portion has become higher, and it is necessary to raise the frequency of the source oscillation clock for the timing generator of the distal end portion. In conjunction with this, the frequency of the transmitted oscillator clock is also raised. As a consequence, if the oscillator clock is transmitted using a fine-wire coaxial cable, the signal quality of the clock deteriorates before it reaches the distal end portion, and there is a possibility that operations of the system will be destabilized. There may also be instances of increased noise radiation due to higher harmonic waves.

In Japanese Patent Application, First Publication No. 2009-45113 a method has been proposed in which, using a twisted pair cable, a high-speed oscillator clock is transmitted by means of a differential digital signal. According to this method, because the clock signal has a small amplitude, relatively high-speed signal can be transmitted, and it is also possible to reduce noise radiation.

Moreover, if a system such as that described in, for example, Japanese Patent Application, First Publication No. 2008-154934 in which video signals undergo A/D conversion in the distal end portion, and are transmitted as digital signals is considered, then the timing signals which are necessary within the circuit in the distal end portion become considerably faster and an extremely high level of accuracy is sought in the base clock on the basis of which such timing signals are generated. As a consequence of this, there is a possibility that the oscillator clock which is transmitted by means of a twisted pair cable will not have sufficient accuracy. Moreover, if the clock having the required speed cannot be obtained using the transmitted oscillator clock, then a multiplier circuit may be provided in the timing generator in the distal end portion and a high-speed clock is created from the transmitted base clock, however, depending on the type of multiplier circuit used, there may be instances in which the clock signal quality becomes even more deteriorated.

A multiplier circuit is generally formed by a phase synchronization circuit having a feedback mechanism which uses a phase-locked loop (PLL) or a delay-locked loop (DLL) (see, for example, FIG. 7 in Japanese Patent Application, First Publication No. 2004-221962, and FIG. 12 in Japanese Patent Application, First Publication No. H10-215153). Such phase synchronization circuits are divided into a type in which all of the systems that make up the feedback mechanism are formed within the same integrated circuit (i.e., an all-digital type), and a type in which a portion of the systems of the feedback mechanism is formed as a separate device thereby enabling highly accurate signals to be obtained (i.e., an external attachment type). In such phase synchronization circuits, if noise and the like become superimposed on the wiring of the feedback systems (i.e., on the wiring forming the feedback loop) so that the signal periodicity is disturbed, then there is a possibility that the synchronization will be out and that the circuit operations will become destabilized, and in some cases considerable time may be lost until stable operations are restored.

All-digital type circuits have all of the feedback systems formed within the same integrated circuit so that these circuits are consequently small in size. Moreover, because the wiring of the feedback systems is not located outside the integrated circuit in an all-digital type, it is possible to reduce the effects of noise. Typically, all-digital types have poor oscillation characteristics and it is possible that there will be a large amount of jitter (i.e., temporal displacement of the signal). For example, in the PLL of an all-digital type, typically, a ring oscillator (RO) is used as a voltage control oscillator (VCO), however, RO generally have poor jitter characteristics, and there are instances in which, unless the base clock is extremely accurate, it is difficult to handle high-frequency signals.

In external attachment types, for example, in a PLL, by employing a highly accurate, externally attached voltage control crystal oscillator (VCXO) as the VCO, it is possible to greatly improve the oscillation characteristics. However, as a result of using a separate device, the size easily increases and the wiring that connects the feedback systems together also extends outside the integrated circuit so that, in some instances, the effects of noise also increase. Size limitations make it impossible to provide a strong magnetic shield, and the fact that this external attachment type of multiplier circuit is located in the distal end portion where it is difficult to avoid the effects of surrounding noise sources means there is a possibility that the system might become destabilized. Note that in medical environments in which an endoscope is used, devices that generate excessive noise such as electrosurgical units and the like are operating at the same time as the endoscope is being used. Consequently, noise is scattered around at a level not present in normal environments, and the effects of such noise are extremely large.

SUMMARY OF THE INVENTION

It is an object of the present invention to provide an endoscope system that makes it possible to stably supply highly accurate clocks to a distal end portion.

An endoscope system according to a first aspect of the present invention is provided with: a distal end portion which is inserted inside a specimen and which has an imaging section that creates video signals, a video signal processing section that processes the video signals from the imaging section, a video transmitting section that transmits the video signals processed by the video signal processing section, a timing signal creation section that creates a timing signal that is needed to drive the imaging section, the video signal processing section, or the video transmitting section, and a base clock receiving section that receives as an optical signal a base clock which is the basis of the timing signal and then converts the received optical signal into an electrical signal; and an external apparatus which has an insertion portion which guides the distal end portion into the specimen, a monitor that displays the video signals, and a video processor that processes the video signals from the distal end portion and outputs them to the monitor. The external apparatus includes a base clock creation section that creates the base clock using a phase synchronization circuit that has a feedback mechanism, and a base clock transmitting section that converts the base clock into an optical signal and transmits the optical signal to the base clock receiving section. The phase synchronization circuit is contained solely within the external apparatus.

Moreover, an endoscope system according to a second aspect of the present invention is provided with: a distal end portion which is inserted inside a specimen and which has an imaging section that creates video signals, a video signal processing section that processes the video signals from the imaging section, a video transmitting section that transmits the video signals processed by the video signal processing section, a timing signal creation section that creates a timing signal that is needed to drive the imaging section, the video signal processing section, or the video transmitting section, and a base clock receiving section that receives as an optical signal a base clock which is the basis of the timing signal and then converts the received optical signal into an electrical signal; and an external apparatus which has an insertion portion which guides the distal end portion into the specimen, a monitor that displays the video signals, and a video processor that processes the video signals from the distal end portion and outputs them to the monitor. The external apparatus includes a base clock creation section that creates the base clock, and a base clock transmitting section that converts the base clock into an optical signal and transmits the optical signal to the base clock receiving section. The distal end portion includes a phase synchronization circuit that has a feedback mechanism, and all of the systems that make up the feedback mechanism are constructed within the same integrated circuit.

In this case, it is also possible for the video signal processing section to convert the video signal from the imaging section into a digital signal, and for the video transmitting section to transmit the video signal as a digital optical signal.

Moreover, in this case, it is also possible for the frequency of the base clock to be set substantially the same as the maximum frequency of the timing signal, or as substantially one half of this maximum frequency.

Moreover, in this case, it is also possible for the external apparatus to be further provided with a connector portion which is connected to the insertion portion and can be removably attached to the video processor section, and for the base clock transmitting section to be placed in the connector portion.

Moreover, in this case, it is also possible for the base clock creation section to be placed in the connector portion.

Moreover, in this case, it is also possible for the external apparatus to be further provided with an operating section that is located in the insertion portion and operates the distal end portion, and for the base clock transmitting section to be placed within the operating section.

Moreover, in this case, it is also possible for the base clock creation section to be placed within the operating section.

DESCRIPTION OF THE PREFERRED EMBODIMENTS

Hereinafter, embodiments of the present invention will be described with reference made to the drawings.

(First Embodiment)

Figure 1:
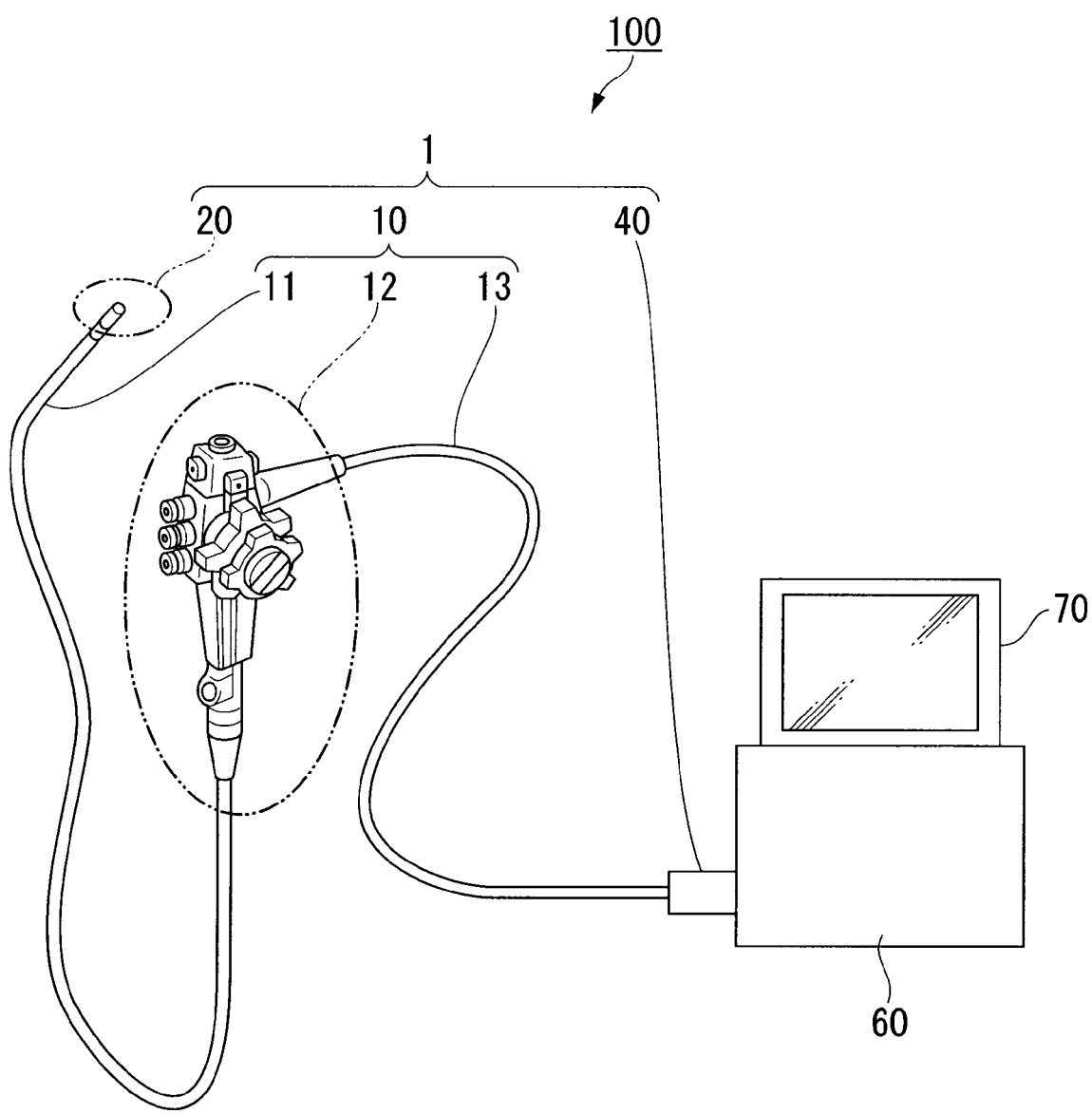
FIG. 1 is an external view of an endoscope system according to a first embodiment of the present invention.

FIG. 1 shows an outline of the structure of an endoscope system 100 according to a first embodiment. As is shown in FIG. 1, the endoscope system 100 is provided with an endoscope scope 1, a video processor 60 which processes video signals acquired by the endoscope scope 1, and a monitor 70 which displays as images video signals processed by the video processor 60.

The endoscope scope 1 of the present embodiment is a scope for medical use and is inserted inside a specimen body cavity. The endoscope scope 1 is provided with a distal end portion 20 which is inserted inside the body cavity and takes video of a target portion inside the body cavity, and then transmits a video signal to the video processor 60, an insertion portion 10 which has a flexible cord and guides the distal end portion 20 to the target portion inside the body cavity, and a connector portion 40 which is used to connect the insertion portion 10 to the video processor 60.

Moreover, the insertion portion 10 is provided with a distal end side insertion portion 11 which is in the form of a flexible cord joined to the distal end portion 20, an operating section 12 which is used to control movements of the distal end portion 20 via the distal end side insertion portion 11, and a connector side insertion portion 13 which is in the form of a flexible cord joining the operating section 12 to the connector portion 40. The external surface of the distal end portion 20 is formed from a hard substance such as, for example, a metal or the like in order to properly protect various mechanisms (described below), and thereby the distal end portion 20 has less flexibility than the distal end side insertion portion 11.

Figure 2:
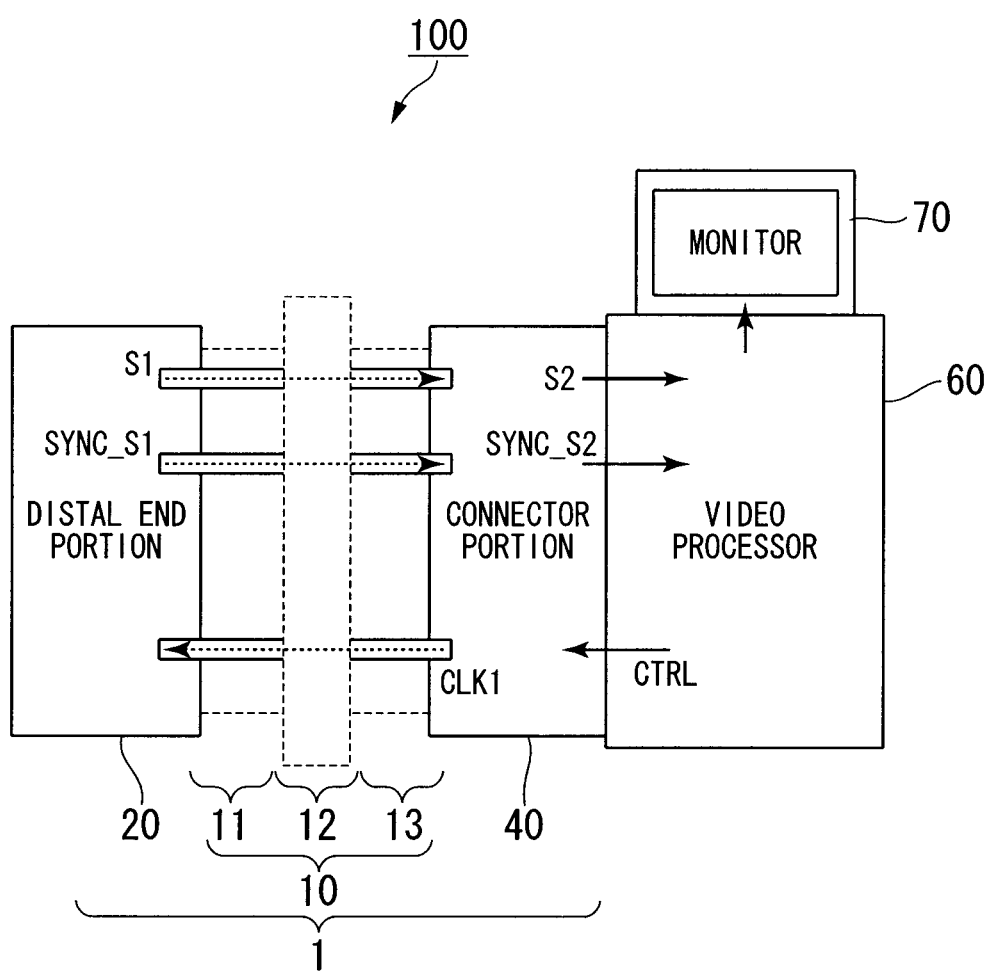
FIG. 2 is a block diagram showing an outline of the functions of the endoscope system according to the first embodiment of the present invention.

FIG. 2 shows function blocks of the endoscope system 100 and the flow of signals thereof. The flow of signals between each function block will now be described with reference made to FIG. 2.

Based on a control signal CTRL from the video processor 60, a clock CLK1 having the maximum frequency of the timing signal required in the distal end portion 20 (i.e., the same frequency as that of a sampling clock SYNC_S1 of a digital video signal S1 output from the distal end portion 20 (described below)) is created in the connector portion 40.

After the created clock CLK1 has undergone E/O conversion (in which electrical signals are converted into optical signals), it is optically transmitted to the distal end portion 20 via an optical fiber inserted through the insertion portion 10.

In the distal end portion 20, an imaging section and the like are driven based on the clock CLK1 which has undergone O/E conversion (in which optical signals are converted into electrical signals). In the distal end portion 20, the digital video signal S1 which has been serialized, and the sampling clock SYNC_S1 which has been synchronized with the digital video signal S1 and is used to sample the digital video signal S1 are created. The digital video signal S1 and the sampling clock SYNC_S1 then undergo E/O conversion, and are subsequently optically transmitted to the connector portion 40 via an optical fiber inserted through the insertion portion 10.

In the connector portion 40, based on the O/E converted sampling clock SYNC_S1 the serialized digital video signal S1 is sampled and a bus signal S2 which is obtained by restoring the sampled video signal to a parallel signal, and a sampling clock SYNC_S2 which has been synchronized with the bus signal S2 and is used to sample the bus signal S2 are created. The bus signal S2 and the sampling clock SYNC_S2 are then transmitted to the video processor 60 via a fine-wire coaxial cable.

The video processor 60 samples the bus signal S2 based on the sampling clock SYNC_S2, and displays video on the monitor 70.

Figure 3:
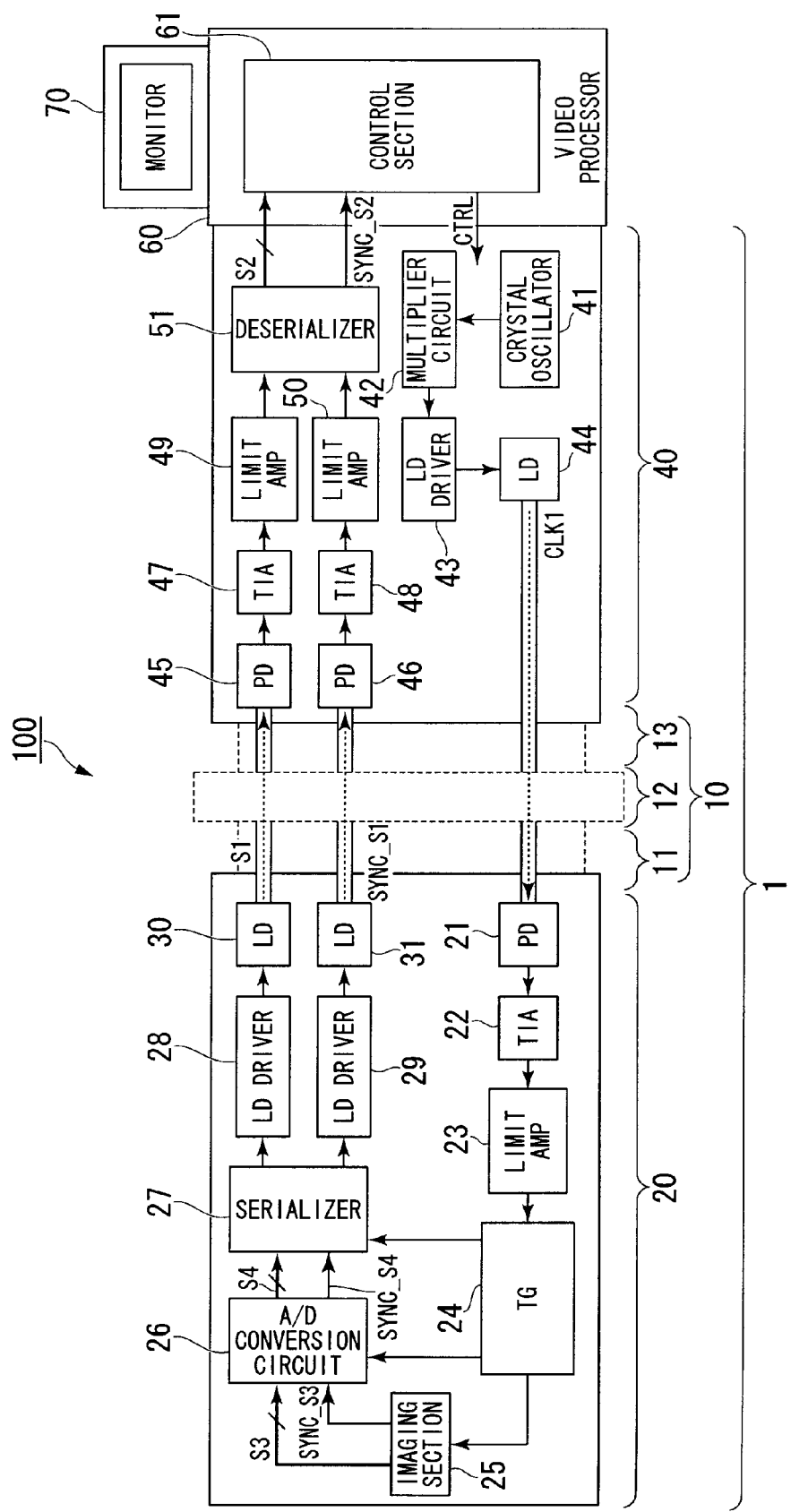
FIG. 3 is a block diagram showing details of the functions of the endoscope system according to the first embodiment of the present invention.

FIG. 3 is a block diagram showing in detail the interior of the function blocks shown in FIG. 2. Operations of the present embodiment will now be described in detail with reference made to FIG. 3. The distal end portion 20 is provided with a photodiode (hereinafter, described as a PD) 21, a trans impedance amplifier (hereinafter, described as a TIA) 22, a limit amplifier 23, a timing generator (hereinafter, described as a TG) 24, an imaging section 25, an A/D conversion circuit 26, a serializer 27, laser diode drivers (hereinafter, described as LD drivers) 28 and 29, and laser diodes (hereinafter, described as LD) 30 and 31. The connector portion 40 is provided with a crystal oscillator 41, a multiplier circuit 42, an LD driver 43, an LD 44, PDs 45 and 46, TIAs 47 and 48, limit amplifiers 49 and 50, and a deserializer 51. Operations of the distal end portion 20 and the connector portion 40 are described in detail below.

The video processor 60 is provided with a control section 61 which controls the overall endoscope system 100. The control section 61 is connected to both the connector portion 40 and the monitor 70. The LD 30 and the PD 45 are connected via an optical fiber which is inserted through the insertion portion 10. A structure such as that shown, for example, in FIG. 4 through FIG. 6 may be considered for the connection structure between the LD 30 and the PD 45.

Figure 4:
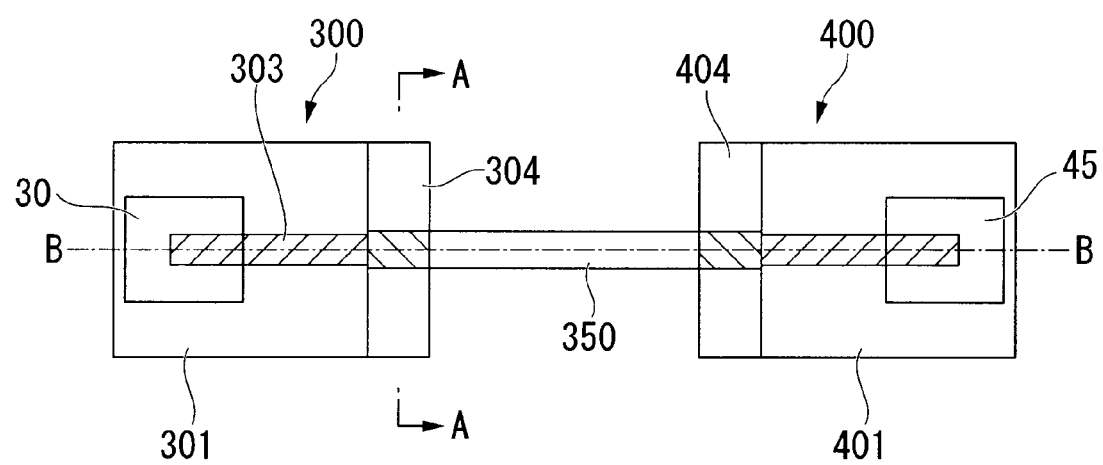
FIG. 4 is a plan view showing a connection structure according to a first embodiment of the present invention.
Figure 5:
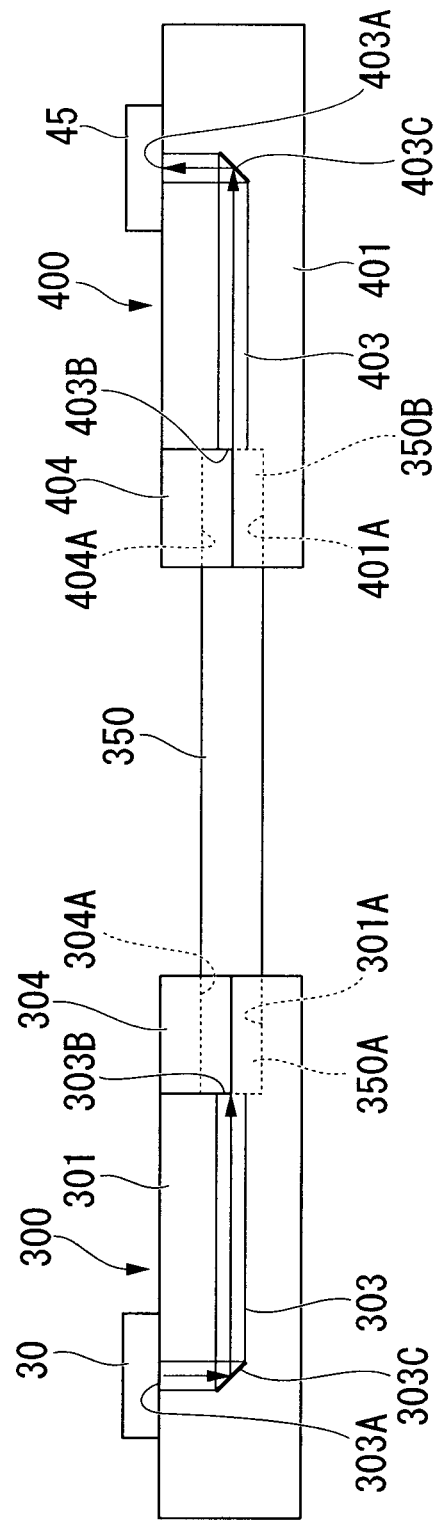
FIG. 5 is a cross-sectional view showing a connection structure according to a first embodiment of the present invention.
Figure 6:
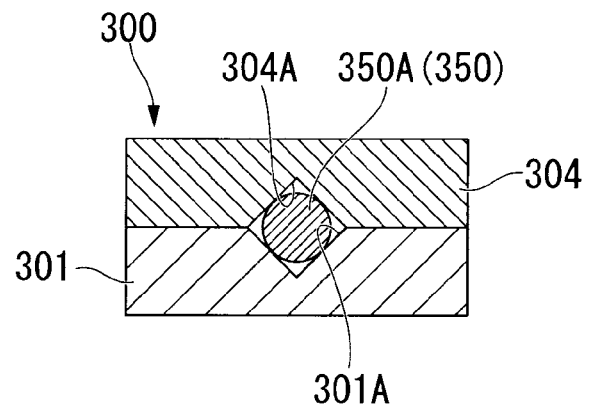
FIG. 6 is a cross-sectional view showing a connection structure according to a first embodiment of the present invention.

FIG. 4 is a plan view showing the connection structure between a first connecting portion 300 in which the LD 30 is connected to an optical fiber, and a second connecting portion 400 in which the PD 45 is connected to the optical fiber. FIG. 5 is a cross-sectional view taken along a line B-B shown in FIG. 4. FIG. 6 is a cross-sectional view taken along a line A-A shown in FIG. 4. Note that the structures inside the first connecting portion 300 and the second connecting portion 400 cannot actually be viewed from outside these components, however, FIG. 4 has been drawn as a transparent view in order to make these structures easier to understand.

As is shown in FIG. 4, the first connecting portion 300 is provided with a plate-shaped optical waveguide path 301 which transmits optical signals from the LD 30, and a guide block 304 which fixes in position an end portion of an optical fiber 350 which is connected to the optical waveguide path 301. The optical waveguide path 301 has a core 303 through which light passes and, as is shown in FIG. 5, the LD 30 is connected to one end surface 303A of the core 303 which has been exposed at a top surface of the optical waveguide path 301.

Moreover, as is shown in FIG. 5 and FIG. 6, a V-groove 301A is formed in the optical waveguide path 301 so as to make contact with the other end surface 303B of the core 303, and one end portion 350A of the optical fiber 350 is disposed in the V-groove 301A. The optical fiber 350 is positioned by the V-groove 301A such that the optical axis thereof coincides with that of the core 303, and the end surface 303B of the core 303 is connected to the end surface 350A of the optical fiber 350. The guide block 304 has a V-groove 304A which is substantially the same as the V-groove 301A and, as is shown in FIG. 6, the guide block 304 is joined to the optical waveguide path 301 so as to cover the top side of the end portion 350A of the optical fiber 350 which is disposed in the V-groove 301A. In this manner, the end surface 350A of the optical fiber 350 is supported such that the optical axis thereof does not become displaced relative to the core 303.

The structure of the second connecting portion 400 is substantially the same as that of the first connecting portion 300, and the second connecting portion 400 is provided with an optical waveguide path 401 and a guide block 404. The PD 45 is connected to one end surface 403A of the core 403 which is exposed at the top surface of the optical waveguide path 401, while the other end portion 350B of the optical fiber 350 is disposed in a V-groove 401A formed in the optical waveguide path 401, and is coaxially connected to the other end surface 403B of the core 403. The top side of the end portion 350B of the optical fiber 350 is covered by the guide block 404 which has the V-groove 404A.

In the first connecting portion 300 which is constructed in the manner described above, optical signals emitted from the LD 30 enter the core 303 from the end surface 303A of the core 303, and are then bent 90° by a reflective surface 303C so that they arrive at the end surface 303B. Next, these optical signals pass through the optical fiber 350 and enter the second connecting portion 400. In the second connecting portion 400, these optical signals enter the core 403 from the end surface 403B of the core 403, and are then bent 90° by a reflective surface 403C so that they reach the end surface 403A and arrive at the PD 45.

Note that in the present invention, an example of the connecting structure between the LD 30 and the PD 45 has been described, however, this same structure may also be used for the structures between the LD 31 and the LD 46, and between the LD 44 and the PD 21.

Operations when the endoscope system 100 constructed in the manner described above is in use will now be described with reference made to FIG. 3.

When the endoscope system 100 outputs video signals, the control section 61 outputs the control signal CTRL. In the connector portion 40, the multiplier circuit 42, which is provided with the above described external attachment type of phase synchronization circuit (having a feedback mechanism), receives the control signal CTRL, multiplies the source oscillation clock of the crystal oscillator 41 to a predetermined frequency, and creates the high-accuracy base clock CLK1. The LD driver 43 receives the base clock CLK1 and drives the LD 44. The LD 44 performs E/O conversion on the base clock CLK1 and optically transmits it to the distal end portion 20 via an optical fiber.

In the distal end portion 20, the PD 21 receives the base clock CLK1, which is an optical signal, and converts this optical signal into current. The TIA 22 performs IN conversion (i.e., current-to-voltage conversion) on the current which is based on the base clock CLK1, and the limit amplifier 23 then binarizes this signal and outputs the binarized signal to the TG 24. The TG 24 does not include the aforementioned phase synchronization circuit having a feedback mechanism, and based on this base clock CLK1 which has been converted into an electrical signal, creates timing signals required in the other circuits of the distal end portion 20 (for example, horizontal synchronizing signal and vertical synchronizing signal and the like of the imaging section 25), and outputs these to the respective circuits.

Figure 7:
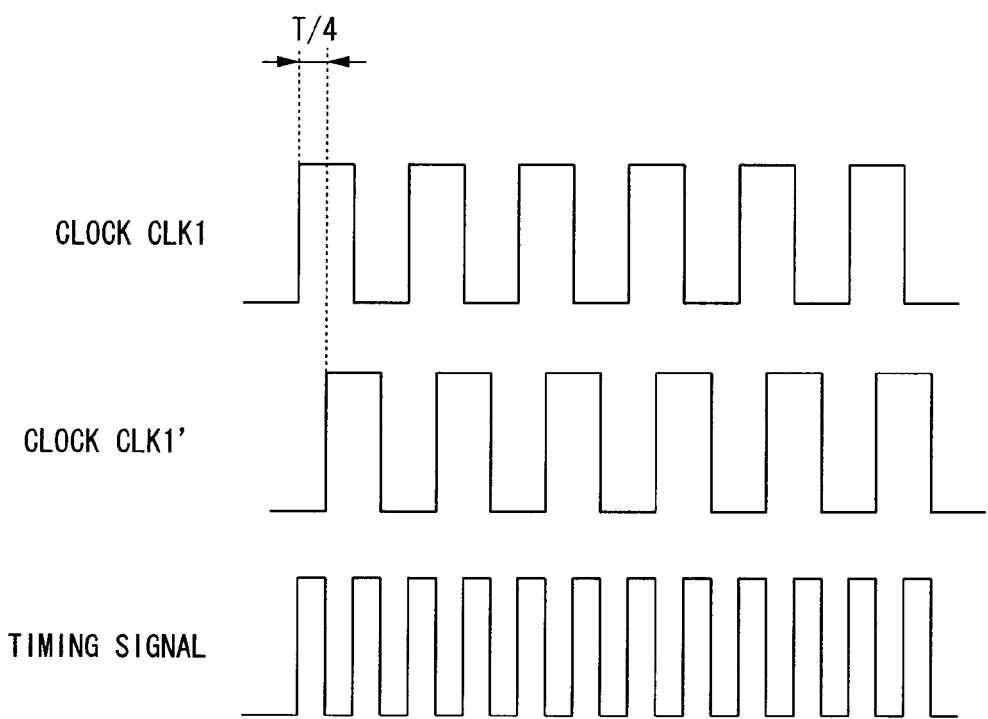
FIG. 7 is a timing chart showing a method of creating timing signals according to a first embodiment of the present invention.

The frequency of the base clock CLK1 is set as either substantially identical to the maximum frequency of the timing signals created by the TG 24, or as one half of this maximum frequency. If the frequency of the base clock CLK1 is one half of the maximum frequency of the timing signals created by the TG 24, the TG 24 creates, for example, a timing signal having the maximum frequency from the base clock CLK1 in the manner described below. FIG. 7 shows the creation of a timing signal having the maximum frequency from the base clock CLK1. Firstly, a clock CLK1' is created by delaying the base clock CLK1 by one fourth of a cycle T using a delay circuit. Next, a timing signal having the maximum frequency is created by XOR operation using the base clock CLK1 and the clock CLK1'. By performing this type of processing, it is possible to create a timing signal having the maximum frequency without using a phase synchronization circuit having a feedback mechanism.

Moreover, by employing, for example, a dividing circuit which uses a counter circuit, the TG 24 is also able to create low frequency timing signals without using a phase synchronization circuit having a feedback mechanism.

In this manner, by obtaining a base clock having substantially the same frequency as the maximum frequency of the created timing signals or having one half the maximum frequency thereof, the TG 24 is able to create the necessary timing signals without using a phase synchronization circuit having a feedback mechanism such as a PLL or a DLL.

As is shown in FIG. 3, the imaging section 25 which is driven by a timing signal from the TG 24 creates and then outputs a video analog bus signal S3, and a sampling clock SYNC_S3 which is synchronized with the bus signal S3. The A/D conversion circuit 26 converts the analog bus signal S3 which has been sampled based on the sampling clock SYNC_S3 into a digital bus signal S4, and then outputs this video digital bus signal S4, and a sampling clock SYNC_S4 which is synchronized with the digital bus signal S4. The serializer 27 converts the digital bus signal S4 which has been sampled based on the sampling clock SYNC_S4 into a serial digital video signal S1, and then outputs this digital video signal S1, and a sampling clock SYNC_S1 which is synchronized with the digital video signal S1. The LD drivers 28 and 29 and the LDs 30 and 31 perform E/O conversion on the digital video signal S1 and the sampling clock SYNC_S1 and then optically transmit these to the connector portion 40 via an optical fiber.

In the connector portion 40, the PDs 45 and 46 convert the digital video signal S1 and the sampling clock SYNC_S1 from optical signals into current. Thereafter, the TIAs 47 and 48 perform IN conversion on the current, the limit amplifiers 49 and 50 then binarize the resulting signals, and convert them into electrical signals. In the deserializer 51, the serial digital video signal S1 is deserialized and is restored to the form of the video digital bus signal S2. This digital bus signal S2 is then output to the video processor 60 from the deserializer 51 together with the sampling clock SYNC_S2 which is synchronized with the digital bus signal S2. In the video processor 60, the control section 61 converts the digital bus signal S2 which has been sampled based on the sampling clock SYNC_S2 into a video signal, and outputs video to the monitor 70.

The endoscope system 100 which is constructed in the manner described above optically transmits the base clock required in TG 24 of the distal end portion. When the base clock is transmitted as an electrical signal, there may be cases in which jitter, which is caused by attenuation and reflection of the electrical signal, is generated, however, by transmitting the base clock as an optical signal, the effects of attenuation and reflection are greatly minimalized. Moreover, because the effects of noise can also be reduced, it is possible to accurately transmit a base clock. In the distal end portion, it is possible to create highly accurate timing signals based on the transmitted high-accuracy clock. As a consequence of this, it becomes possible to transmit video signals at a high transmission rate from the distal end portion. Moreover, as is shown in the present embodiment, by using an optical signal to perform this video signal transmission as well, it is possible to suppress the effects of attenuation, reflection and noise, and it is possible to achieve an endoscope system that outputs video having a high image quality.

Moreover, in the present embodiment, it is possible to create timing signals without employing in the distal end portion which is easily affected by peripheral noise sources a phase synchronization circuit which has a feedback mechanism in which there is a possibility that the synchronization will be affected by noise and the like and become offset so that the operation will become destabilized, and which will require considerable time until stable operations can be restored. Because of this, it is possible to achieve a highly stable endoscope system.

Note that in the present embodiment, the TG 24 does not include a phase synchronization circuit having a feedback mechanism, however, it is also possible to use for the TG 24 the above-described all-digital type of phase synchronization circuit in which all of the systems making up the feedback mechanism are formed within the same integrated circuit. In this case, it is possible to construct a multiplier circuit in which the effects of noise are suppressed in the distal end portion, and to easily create a timing signal having the desired frequency from a low-frequency base clock. Note that there is a possibility of increased jitter in an all-digital type of phase synchronization circuit, however, in the present embodiment, as is described above, because the accuracy of the base clock is improved, the effects of this increased jitter can be canceled.

Moreover, adjustment of the optical axis is not easy in optical transmissions, and if removable attachment portions such as connector portions are provided on an optical transmission path, an extremely high level of fitting accuracy is necessary where such portions are located. Above all, in the present embodiment, a situation in which the optical transmitting and receiving portion is located in the connector portion so that the optical transmission path has to pass through a location where the connector portion and the video processor are removably attached to each other is avoided, and it is possible to form the removable attachment location as an electrical connection point and thereby alleviate the need for a high standard of fitting accuracy in the connector portion. Moreover, by locating the base clock creation section which is formed by the crystal oscillator 41 and the multiplier circuit 42 in the connector portion, the base clock does not pass through the removable attachment portion, and because it is no longer affected by signal degradation generated in the removable attachment portions, an even higher level of accuracy can be maintained in the base clock.

Moreover, in the present embodiment, both the digital video signal S1, and the sampling clock SYNC_S1 which is synchronized with the digital video signal S1 and is used to sample the digital video signal S1 are transmitted together. However, it is also possible to embed the sampling clock in the digital video signal using clock data recovery (CDR) technology, and to thus integrate the digital video signal S1 and the sampling clock SYNC_S1.

(Second Embodiment)

Figure 8:
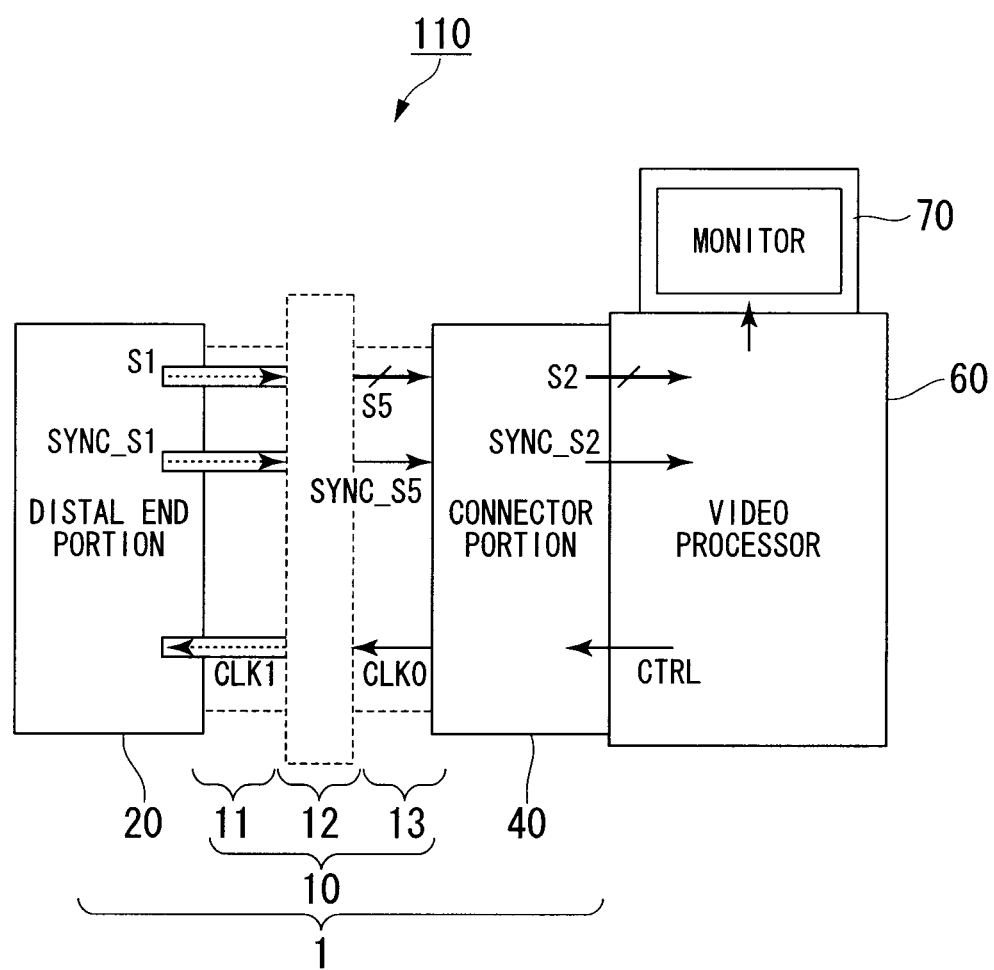
FIG. 8 is a block diagram showing an outline of the functions of an endoscope system according to a second embodiment of the present invention.
Figure 9:
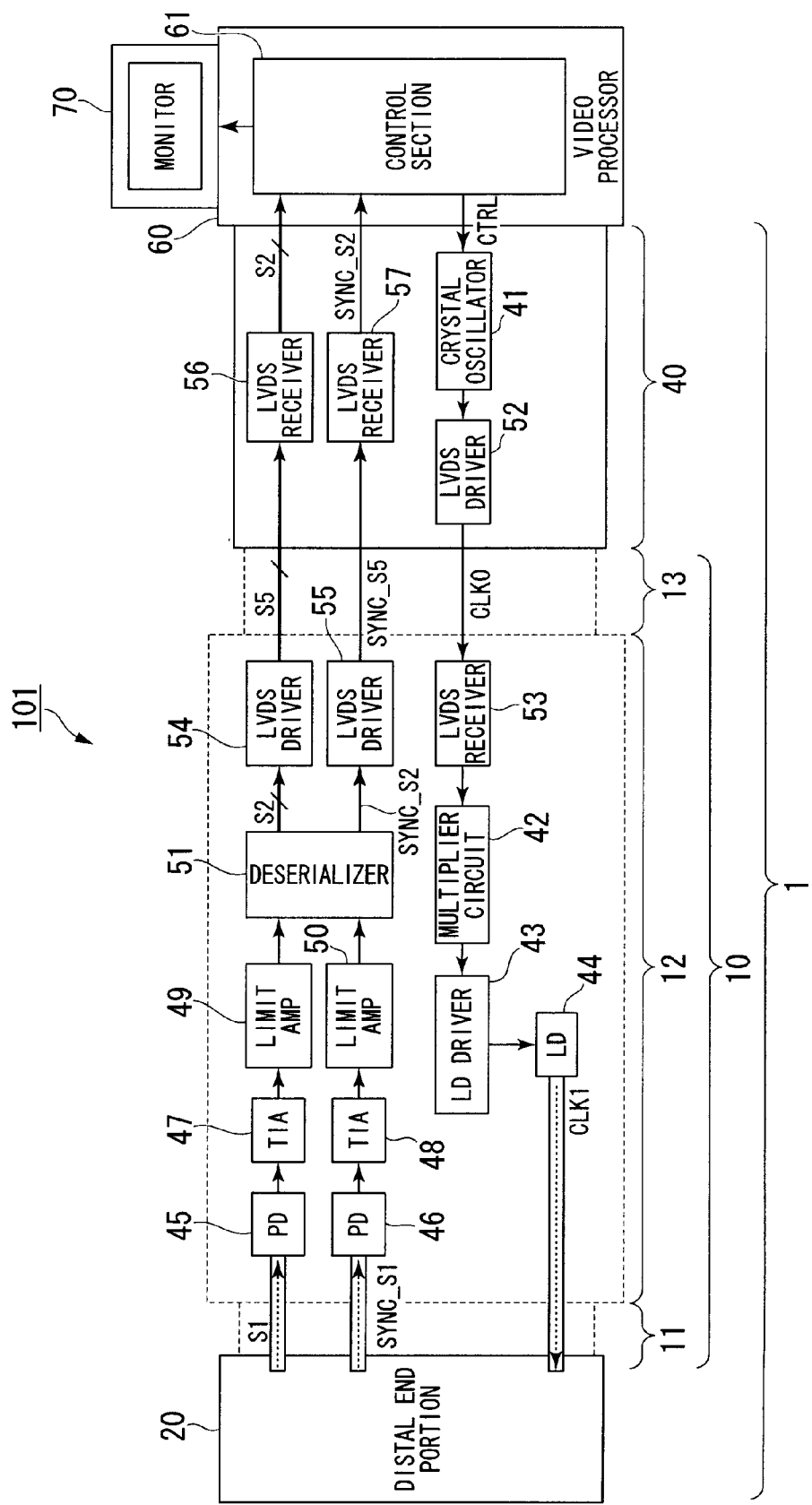
FIG. 9 is a block diagram showing details of the functions of the endoscope system according to the second embodiment of the present invention.

Next, a second embodiment of the present invention will be described with reference made to FIG. 8 and FIG. 9. In FIG. 8 and FIG. 9, the same symbols are used for component elements that are the same as those in the first embodiment and no description of these is given. Instead, only points of difference with the first embodiment are described. In addition, the schematic structure of an endoscope system 110 of the present embodiment is the same as the schematic structure (see FIG. 1) of the endoscope system 100 of the first embodiment.

FIG. 8 shows function blocks of the endoscope system 110 of the second embodiment, and shows the flow of the signals thereof. The flow of signals between each function block will now be described with reference made to FIG. 8. The principal difference with the endoscope system 100 of the first embodiment which is shown in FIG. 2 is that the method used to transmit signals between the operating section 12 and the connector portion 40 is changed from optical transmission to LVDS transmission.

In the connector portion 40, based on the control signal CTRL from the video processor 60, the clock CLK0 from the oscillator is converted into an LVDS signal (i.e., a differential digital signal), and is then transmitted to the operating section 12 via a twisted pair cable. In the operating section 12, the clock CLK1 having the maximum frequency of the timing signals required by the distal end portion 20 is created based on the received clock CLK0. This clock CLK1 then undergoes E/O conversion and is subsequently transmitted via an optical fiber to the distal end portion 20.

In the distal end portion 20, the imaging section and the like are driven based on the O/E converted clock CLK1, and the digital video signal S1 which has been serialized, and the sampling clock SYNC_S1 which has been synchronized with the digital video signal S1 and is used to sample the digital video signal S1 are created. The digital video signal S1 and the sampling clock SYNC_S1 then undergo E/O conversion, and are subsequently optically transmitted to the operating section 12 via an optical fiber.

In the operating section 12, based on the O/E converted sampling clock SYNC_S1 the serialized digital video signal S1 is sampled, and a bus signal S2 which is obtained by restoring the sampled video signal S1 to a parallel signal, and a sampling clock SYNC_S2 which has been synchronized with the bus signal S2 and is used to sample the bus signal S2 are created. Moreover, in the operating section 12, the bus signal S2 and the sampling clock SYNC_S2 are converted into LVDS signals S5 and SYNC-S5, and these are then transmitted via twisted pair cable to the connector portion 40.

In the connector portion 40, the LVDS signals S5 and SYNC-55 are then restored to the form of the simple signals S2 and SYNC_S2, and are then transmitted to the video processor 60 via a fine-wire coaxial cable. The video processor 60 samples the digital video signal S2 based on the sampling clock SYNC_S2, and then displays video on the monitor 70.

FIG. 9 is a block diagram showing in detail the interior of the function blocks shown in FIG. 8. In the present embodiment, a structure is employed in which the block within the connector portion 40 shown in FIG. 3 described in the first embodiment without the crystal oscillator 41 is moved to the operating section 12. Moreover, the operating section 12 and the connector portion 40 are connected by a twisted pair cable, and signals are transmitted by LVDS.

Namely, in the connector portion 40, the clock signal CLK0 created by the crystal oscillator 41 is transmitted as an LVDS signal by an LVDS driver 52 to the operating section 12. In the operating section 12, this LVDS signal is received by an LVDS receiver 53. Moreover, in the operating section 12, the bus signal S2 and the sampling clock SYNC_S2 are converted into LVDS signals 55 and SYNC_S5 by the LVDS drivers 54 and 55, and these are then transmitted to the connector portion 40. In the connector portion 40, the LVDS signals 55 and SYNC 55 are received by the LVDS receivers 56 and 57 where they are once again converted into the bus signal S2 and the sampling clock SYNC_S2.

In the endoscope system 110 having the above described structure, if the optical signal transmitting-receiving section is disposed in the operating section 12 then high-cost optical fibers need to be provided only in the distal end insertion portion 11 alone and, compared with when high-cost optical fibers are provided in the entire insertion portion 10, it is possible to reduce costs. Note that, as is described above, in the present embodiment, because LVDS transmission is employed for signal transmissions of the connector side insertion portion 13 between the connector portion 40 and the operating section 12, the transmission distance is shorter than when LVDS transmission is performed over the entire insertion portion 10, and because the connector side insertion portion 13 is not inserted into the body, the cord thereof can be fatter than it would otherwise be. Accordingly, it is comparatively easy to control any deterioration in signal quality in the connector side insertion portion 13.

Moreover, in the present embodiment, the crystal oscillator 41 and the multiplier circuit 42 are disposed separately in the connector portion 40 and the operating section 12 respectively, however, it is also possible to group these together and place them in the operating section 12. By doing this, it is possible to prevent any signal deterioration that arises in the transmission of signals from the connector portion to the operating section, and the base clock can be kept at an even higher level of accuracy.

Preferred embodiments of the present invention have been described in detail above with reference made to the drawings, however, the specific structure of the present invention is not limited to the above described embodiments and may include design modifications and the like insofar as these do not depart from the spirit or scope of the present invention. For example, an example has been described above in which the present invention is applied to an endoscope system which is used for medical treatment, however, the present invention may also be applied to industrial endoscope systems that are used to monitor industrial products such as pipes and the like.

According to the present invention, because it is possible to create highly accurate timing signals without having to place an external attachment type of phase synchronization circuit in the distal end portion, a highly stable endoscope system can be achieved.

What is claimed is:

1. An endoscope system, comprising:
a distal end portion which is inserted inside a specimen, and
an external apparatus connected to the distal end portion, wherein the distal end portion has
an imaging section that creates video signals,
a video signal processing section that processes the video signals from the imaging section,
a video transmitting section that transmits the processed video signals from the distal end portion to the external apparatus,
a timing signal creation section that creates a timing signal that is needed to drive at least one of the imaging section, the video signal processing section, and the video transmitting section, and
a base clock receiving section that receives a base clock, wherein the base clock is transmitted from the external apparatus to the distal end portion, wherein the base clock is received as an optical signal, wherein the timing signal is created from the base clock, and wherein the base clock receiving section converts the received optical signal into an electrical signal in the distal end portion,
wherein the external apparatus has
an insertion portion which guides the distal end portion into the specimen,
a monitor that displays the video signals,
a video processor that processes the video signals from the distal end portion and outputs them to the monitor,
a base clock creation section that creates the base clock in the external apparatus, using a phase synchronization circuit that has a feedback mechanism, and
a base clock transmitting section that converts the base clock into an optical signal and transmits the optical signal to the base clock receiving section, and
wherein, in the endoscope system, the phase synchronization circuit is contained only within the external apparatus.

2. An endoscope system, comprising:
a distal end portion which is inserted inside a specimen, and
an external apparatus connected to the distal end portion, wherein the distal end portion has
an imaging section that creates video signals,
a video signal processing section that processes the video signals from the imaging section,
a video transmitting section that transmits the processed video signals from the distal end portion to the external apparatus,
a timing signal creation section that creates a timing signal that is needed to drive at least one of the imaging section, the video signal processing section, and the video transmitting section, and
a base clock receiving section that receives a base clock, wherein the base clock is transmitted from the external apparatus to the distal end portion, wherein the base clock is received as an optical signal, wherein the timing signal is created from the base clock, and wherein the base clock receiving section converts the received optical signal into an electrical signal in the distal end portion,
wherein the external apparatus has
an insertion portion which guides the distal end portion into the specimen,
a monitor that displays the video signals,
a video processor that processes the video signals from the distal end portion and outputs them to the monitor,
a base clock creation section that creates the base clock in the external apparatus, and
a base clock transmitting section that converts the base clock into an optical signal and transmits the optical signal to the base clock receiving section, and
wherein the distal end portion includes a phase synchronization circuit that has a feedback mechanism, and all of the systems that make up the feedback mechanism are constructed within the same integrated circuit.

3. The endoscope system according to claim 1, wherein the video signal processing section converts the video signal from the imaging section into a digital signal, and
the video transmitting section transmits the video signal as a digital optical signal.

4. The endoscope system according to claim 2, wherein the video signal processing section converts the video signal from the imaging section into a digital signal, and
the video transmitting section transmits the video signal as a digital optical signal.

5. The endoscope system according to claim 1, wherein the frequency of the base clock is set as the maximum frequency of the timing signal, or as one half of this maximum frequency.

6. The endoscope system according to claim 2, wherein the frequency of the base clock is set as the maximum frequency of the timing signal, or as one half of this maximum frequency.

7. The endoscope system according to claim 1, wherein the external apparatus is further provided with a connector portion which is connected to the insertion portion and can be removably attached to the video processor section, and
the base clock transmitting section is placed in the connector portion.

8. The endoscope system according to claim 2, wherein the external apparatus is further provided with a connector portion which is connected to the insertion portion and can be removably attached to the video processor section, and
the base clock transmitting section is placed in the connector portion.

9. The endoscope system according to claim 7, wherein the base clock creation section is placed in the connector portion.

10. The endoscope system according to claim 8, wherein the base clock creation section is placed in the connector portion.

11. The endoscope system according to claim 1, wherein the external apparatus is further provided with an operating section that is located in the insertion portion and operates the distal end portion, and
the base clock transmitting section is placed within the operating section.

12. The endoscope system according to claim 2, wherein the external apparatus is further provided with an operating section that is located in the insertion portion and operates the distal end portion, and the base clock transmitting section is placed within the operating section.

13. The endoscope system according to claim 11, wherein the base clock creation section is placed within the operating section.

14. The endoscope system according to claim 12, wherein the base clock creation section is placed within the operating section.

* * * * *